United States Patent
Bennett et al.

(10) Patent No.: US 8,725,533 B2
(45) Date of Patent: May 13, 2014

(54) POLICY-DRIVEN RELOCATION OF ELECTRONIC HEALTHCARE RECORDS IN A NETWORK ENVIRONMENT

(75) Inventors: Craig A. Bennett, Woodstock, GA (US); Tomer Kol, Yoqneam-Illit (IL); Richard J. Stevens, Rochester, MN (US); Karen A. Witting, Croton-on-Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 2911 days.

(21) Appl. No.: 11/372,335

(22) Filed: Mar. 9, 2006

(65) Prior Publication Data

US 2007/0214016 A1    Sep. 13, 2007

(51) Int. Cl.
*A61B 5/00* (2006.01)
*G06F 19/00* (2011.01)

(52) U.S. Cl.
USPC ............................................................ 705/3

(58) Field of Classification Search
USPC .......................................................... 705/2, 3
See application file for complete search history.

(56) References Cited

U.S. PATENT DOCUMENTS

| | | | |
|---|---|---|---|
| 6,363,385 B1 * | 3/2002 | Kedem et al. | 707/10 |
| 6,539,425 B1 * | 3/2003 | Stevens et al. | 709/220 |
| 7,080,225 B1 * | 7/2006 | Todd | 711/165 |
| 2002/0099767 A1 * | 7/2002 | Cohen et al. | 709/203 |
| 2002/0107875 A1 * | 8/2002 | Seliger et al. | 707/200 |
| 2002/0152231 A1 * | 10/2002 | Silva-Craig et al. | 707/204 |
| 2004/0034550 A1 * | 2/2004 | Menschik et al. | 705/3 |
| 2005/0021519 A1 * | 1/2005 | Ghouri | 707/9 |
| 2005/0193222 A1 * | 9/2005 | Greene | 713/201 |
| 2005/0195660 A1 * | 9/2005 | Kavuri et al. | 365/189.05 |
| 2006/0047930 A1 * | 3/2006 | Takahashi et al. | 711/162 |
| 2006/0085785 A1 * | 4/2006 | Garrett | 718/1 |
| 2006/0218366 A1 * | 9/2006 | Fukuda et al. | 711/165 |
| 2007/0199047 A1 * | 8/2007 | Gibart et al. | 726/2 |

* cited by examiner

*Primary Examiner* — John Pauls
*Assistant Examiner* — Trang Nguyen
(74) *Attorney, Agent, or Firm* — Patterson & Sheridan LLP (57) ABSTRACT

A method and apparatus for storing electronic healthcare records is disclosed. Embodiments of the invention provide techniques for managing electronic healthcare records in a hybrid domain that includes a high-availability centralized data store and set of distributed data nodes. A set of location policies may be used to determine whether to store an electronic healthcare record in the centralized data store. Over time, events may occur that trigger certain data records to be relocated from the plurality of distributed database nodes to the centralized data store.

23 Claims, 5 Drawing Sheets

POLICY-DRIVEN RELOCATION OF ELECTRONIC HEALTHCARE RECORDS IN A NETWORK ENVIRONMENT

BACKGROUND OF THE INVENTION

1. Field of the Invention

The present invention generally relates to computer databases used to store electronic records. More specifically, the present invention relates to managing the accessibility of electronic healthcare records in a distributed domain.

2. Description of the Related Art

When an individual visits a physician, hospital, or clinic, numerous records related to the visit may be created. Records such as lab results, x-rays and other images, prescriptions, and notes regarding treatment decisions, provide a few common examples of records that may be created as a result of a treatment encounter between a patient and a physician. Such records also often reflect the diagnosis of some disease or condition along with a prescribed course of treatment. Historically, the records related to a particular individual or treatment encounter have been maintained by the provider responsible for creating the record. For example, an individual's primary care physician typically maintains any records related to treatment encounters between the individual and the primary care physician. Thus, when an individual visits the primary care physician for an annual physical exam, the records related to the exam are created and stored at the office of the primary care physician. Similarly, if an individual receives care at an emergency room, the attendant hospital has historically maintained records of the care provided at the emergency room.

Like records maintained for virtually every other profession, healthcare records have begun to migrate from paper to electronic forms, and computer databases are frequently used to store electronic healthcare records. Computer databases are well known systems used to store, maintain, and retrieve data. Generally, a database is a collection of data that is organized in a manner to allow its contents to be easily accessed, managed, and updated. The most prevalent type of database used today is the relational database, which organizes data using tables, and relationships between tables. For example, the DB2® family of RDBMS products (relational database management system) available from International Business Machines (IBM) provides a sophisticated commercial implementation of a relational database.

As more and more health care providers are turning to computer databases and practice management applications to create, store, and manage patient data, the ability of providers to share electronic records with one another has become increasingly viable. Accordingly, a great deal of interest has been focused on creating regional, national, and even global networks of shared access to electronic healthcare records, and many initiatives and pilots programs are either underway or being considered. The general goal of these projects is to provide a physician rendering treatment with access to all of the relevant electronic records for a patient, regardless of the location of the records or the healthcare provider involved in treatment.

A number of network models have been proposed to use in providing physicians with shared access to healthcare records. At one end of the spectrum is a fully centralized approach where the data records for a group of providers is stored using a data warehouse model. In a data warehouse model, data records created by many providers are stored in a centralized data center that may accessed by each of the providers. An advantage of this approach is that the data center may be optimized to meet specific quality of service targets (e.g. performance, availability, backup/recovery). At the same time, however, this model requires broad agreement among providers that all data records will be managed by a central authority; a requirement that may not be practical for electronic healthcare records. For example, issues over privacy concerns may prevent deployment of a single, nationwide electronic health record warehouse. Moreover, the scaling and reliability issues associated with a single warehouse approach are daunting. Consider, for example, how large such a warehouse would be that would contain all healthcare records for all citizens in a country as large as the United States.

At the other end of the spectrum is a fully distributed or federated approach. A federated model integrates multiple, heterogeneous, data sources. This approach allows each provider to access records distributed across multiple database management systems as though they were stored locally at the provider. Using this approach, electronic records regarding a given patent patient may be assembled on demand to provide a complete healthcare history of the individual. However, one drawback to using a fully federated model is that users may experience inconsistent quality of service levels provided by the diverse set of data sources. Moreover, many providers may be unwilling (or unable) to manage a local infrastructure with reasonable quality of service levels. Thus, issues such as partial failures due to network connectivity and/or (un)scheduled down time may prevent a fully federated approach from being a workable approach to sharing access to electronic healthcare records.

In between these extremes are hybrid approaches where some records may be centralized across local, state, or even national boundaries and others are stored in distributed or federated data stores. When new records are created, they may be stored in either a centralized or a local data store; however, problems may arise in deciding whether to store a particular record in a centralized or local data store. Moreover, the relative importance of a particular electronic healthcare record may change with the occurrence of contemporaneous events. Accordingly, there remains a need for techniques to manage electronic healthcare records stored using a hybrid approach; one that leverages the advantages of a centralized warehouse and the high-availability services it may provide, while still allowing at least some portion of the electronic records to remain federated across a number of distributed data nodes.

SUMMARY OF THE INVENTION

Embodiments of the invention provide techniques for intelligently relocating data from a collection of federated data sources to a centralized warehouse. One embodiment of the invention provides a computer-implemented method of selecting a location to store an electronic record, the method generally includes receiving the electronic record from one of a plurality of health care providers, wherein each of the plurality of health care providers maintains a local data store of electronic records, and wherein the plurality of health care providers have shared access to a centralized data store, retrieving a set of data location policies used to determine which electronic records are to be accessible from the centralized data store, and evaluating the electronic record, based on the data location policies, to determine whether the electronic record should be accessible from the centralized data store. If so, the method generally further includes storing the electronic record in the centralized data store and updating a data location registry to indicate the location of the electronic record.

Another embodiment of the invention provides a computer-readable medium containing a program which, when executed, performs an operation for selecting a location to store an electronic record. The operation generally includes, receiving the electronic record from one of a plurality of health care providers, wherein each of the plurality of health care providers maintains a local data store of electronic records, and wherein the plurality of health care providers have shared access to a centralized data store, retrieving a set of data location policies used to determine which electronic records are to be accessible from the centralized data store, and evaluating the electronic record, based on the data location policies, to determine whether the electronic record should be accessible from the centralized data store. If so, the operation generally further includes, storing the electronic record in the centralized data store and updating a data location registry to indicate the location of the electronic record.

Still another embodiment of the invention includes a system for storing electronic records, the system generally includes a centralized data store having respective communication links to a plurality of local data stores each maintaining electronic records, wherein each of the local data stores is maintained by a respective health care provider, each having access to electronic records stored in the centralized data store, and a data access manager configured to determine whether to store an electronic record, received from one of the health care providers, in the centralized data store.

Still another embodiment of the invention includes computer-implemented method of providing accessibility to electronic records. The method generally includes, providing a centralized data store having communication links with a plurality of health care providers, wherein each of the plurality of health care providers maintains a local data store of electronic records, and wherein the plurality of health care providers have shared access to the centralized data store. The method generally further includes managing the accessibility of the electronic records from the centralized data store by selectively storing the electronic records of the local data stores at the centralized data store, so that each of the local data stores have access to the electronic records at the centralized data store; wherein the accessibility is managed on the basis of predefined events which cause a data manager of the centralized data store to make the electronic records of the local data stores available at the centralized data store and subsequently make the electronic records of the local data stores unavailable at the centralized data store.

Still another embodiment of the invention provides a computer-implemented method of accessing electronic records. The method generally includes receiving, by a computer of a first health care provider, a request from a centralized data store for local electronic records stored by the computer of the first health care provider, wherein the centralized data store has communication links with respective computers of a plurality of health care providers inclusive of the first health care provider. Additionally, each of the plurality of health care providers may maintain a local data store of electronic records, the plurality of health care providers may have shared access to the centralized data store, and the centralized data store may manage the accessibility of the electronic records from the centralized data store by selectively storing the electronic records of the local data stores at the centralized data store. Further, according to the method of this embodiment, each of the plurality of health care providers may have access to the electronic records at the centralized data store, wherein the accessibility is managed on the basis of predefined events which cause a data manager of the centralized data store to make the electronic records of the respective local data stores available at the centralized data store and subsequently make the electronic records of the local data stores unavailable at the centralized data store. The method generally further includes providing the requested local electronic records to the centralized data store.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments of the invention illustrated in the appended drawings.

Note, however, that the appended drawings illustrate only typical embodiments of this invention and are therefore not to be considered limiting of its scope, for the invention may admit to other equally effective embodiments.

DETAILED DESCRIPTION OF THE PREFERRED EMBODIMENTS

Embodiments of the present invention provide techniques for managing electronic healthcare records in a hybrid domain that includes a centralized data store and set of distributed data nodes. In one embodiment, a management application (referred to herein as a "data location manager") may be responsible for selecting certain electronic records to store in the centralized data store. Such a data store may be located at a data center configured to provide a high-availability, fault-tolerant store of electronic healthcare records accessed by multiple providers. However, storing records at the high-availability data center may be more costly than storing electronic records at a number of distributed nodes of a data federation. Accordingly, less critical electronic healthcare records may be stored at distributed nodes of the federated database. In one embodiment, each node of the data federation may comprise a data store managed by a hospital, clinic, or other health care goods/services providing organization. As new electronic healthcare records are created by a health care provider, the data location manager may be configured to determine where the record should be located.

However, the importance of having certain electronic healthcare records available from the centralized data store may change under some circumstances. Consider the following example: the majority of electronic healthcare records regarding a particular individual are located at the offices of a private physician, and stored in a local data store. The local data sore may be part of a larger federation, allowing other health care providers to access the records related to the individual. Consider, however, what should happen if this individual is treated at an emergency room, or scheduled to be admitted to a hospital for a surgical procedure. Under such circumstances, high-reliability access to the individual's records may be very important to physicians at the hospital. In such a case, the individual's admission to the hospital may trigger the data location manager to move (or replicate) at least some of records stored in the distributed node to the centralized data store. After a certain period of time, however, the importance of these records may "expire," e.g., after the individual has recovered and is discharged from the hospital. When this occurs, guaranteed on-demand access to the individual's records may no longer be of high importance. To address this situation, the data location manager may specify an eviction time for the electronic healthcare records temporarily relocated to the data center.

Additional examples of scenarios where it may be appropriate to relocate electronic healthcare records are discussed below; including examples of moving electronic records from a centralized data store to a distributed node (referred to as "record eviction") and the reverse action of moving electronic records from a distributed node to the centralized data store (referred to as "record promotion"). Additionally, although described herein as "moving" data records from one location to another, those skilled in the art will recognize that "moving" may include making copies of electronic data records, in which case it is also contemplated that appropriate version control (including document lock-out) and/or synchronization protocols may be employed.

Additional situations arise where it may be appropriate to relocate records to (or from) the centralized data store and a distributed node. For example, the capacity (or the cost) of storing data at the data center may itself change. Similarly, some providers (or individuals) may be willing to pay a premium to have certain records stored in the high availability data center. Further, the data relocation policies may change, allowing more (or fewer) records to be stored at the high-availability data center.

In the following, reference is made to embodiments of the invention. However, it should be understood that the invention is not limited to any specifically described embodiments. Instead, any combination of the following features and elements, whether related to different embodiments or not, is contemplated to implement and practice the invention. Furthermore, in various embodiments the invention provides numerous advantages over the prior art. However, although embodiments of the invention may achieve advantages over other possible solutions and/or over the prior art, whether or not a particular advantage is achieved by a given embodiment is not limiting of the invention. Thus, the following aspects, features, embodiments and advantages are merely illustrative and are not considered elements or limitations of the appended claims except where explicitly recited in a claim(s). Likewise, reference to "the invention" shall not be construed as a generalization of any inventive subject matter disclosed herein and shall not be considered to be an element or limitation of the appended claims except where explicitly recited in a claim(s).

Further, embodiments of the invention may be implemented using computer software applications executing on existing computer systems, e.g., desktop computers, server computers, laptop computers, tablet computers, and the like.

The software applications described herein, however, are not limited to any currently existing computing environment or programming language, and may be adapted to take advantage of new computing systems as they become available. Additionally, the components illustrated in FIGS. 1-3 may be implemented as software applications executing on individual computer systems or distributed systems communicating over computer networks, including local area networks or large, wide area networks, such as the Internet One embodiment of the invention is implemented as a program product for use with a computer (i.e., as a computer software application or applications). The program(s) of the program product defines functions of the embodiments (including the methods described herein) and can be contained on a variety of computer-readable media. Illustrative computer-readable media include, but are not limited to: (i) information permanently stored on non-writable storage media (e.g., read-only memory devices within a computer such as CD-ROM and DVD disks readable by a CD-ROM drive and DVD drive, respectively); (ii) alterable information stored on writable storage media (e.g., floppy disks within a diskette drive or hard-disk drive); or (iii) information conveyed to a computer by a communications medium, such as through a computer or telephone network, including wireless communications. The latter embodiment specifically includes information to/from the Internet and other networks. Such computer-readable media, when carrying computer-readable instructions that direct the functions of the present invention, represent embodiments of the present invention.

In general, the routines executed to implement the embodiments of the invention, may be part of an operating system or a specific application, component, program, module, object, or sequence of instructions. The computer program of the present invention typically is comprised of a multitude of instructions that will be translated by the native computer into a machine-readable format and hence executable instructions. Also, programs are comprised of variables and data structures that either reside locally to the program or are found in memory or on storage devices. In addition, various programs described hereinafter may be identified based upon the application for which they are implemented in a specific embodiment of the invention. However, it should be appreciated that any particular program nomenclature that follows is used merely for convenience, and thus the invention should not be limited to use solely in any specific application identified and/or implied by such nomenclature.

Figure 1:
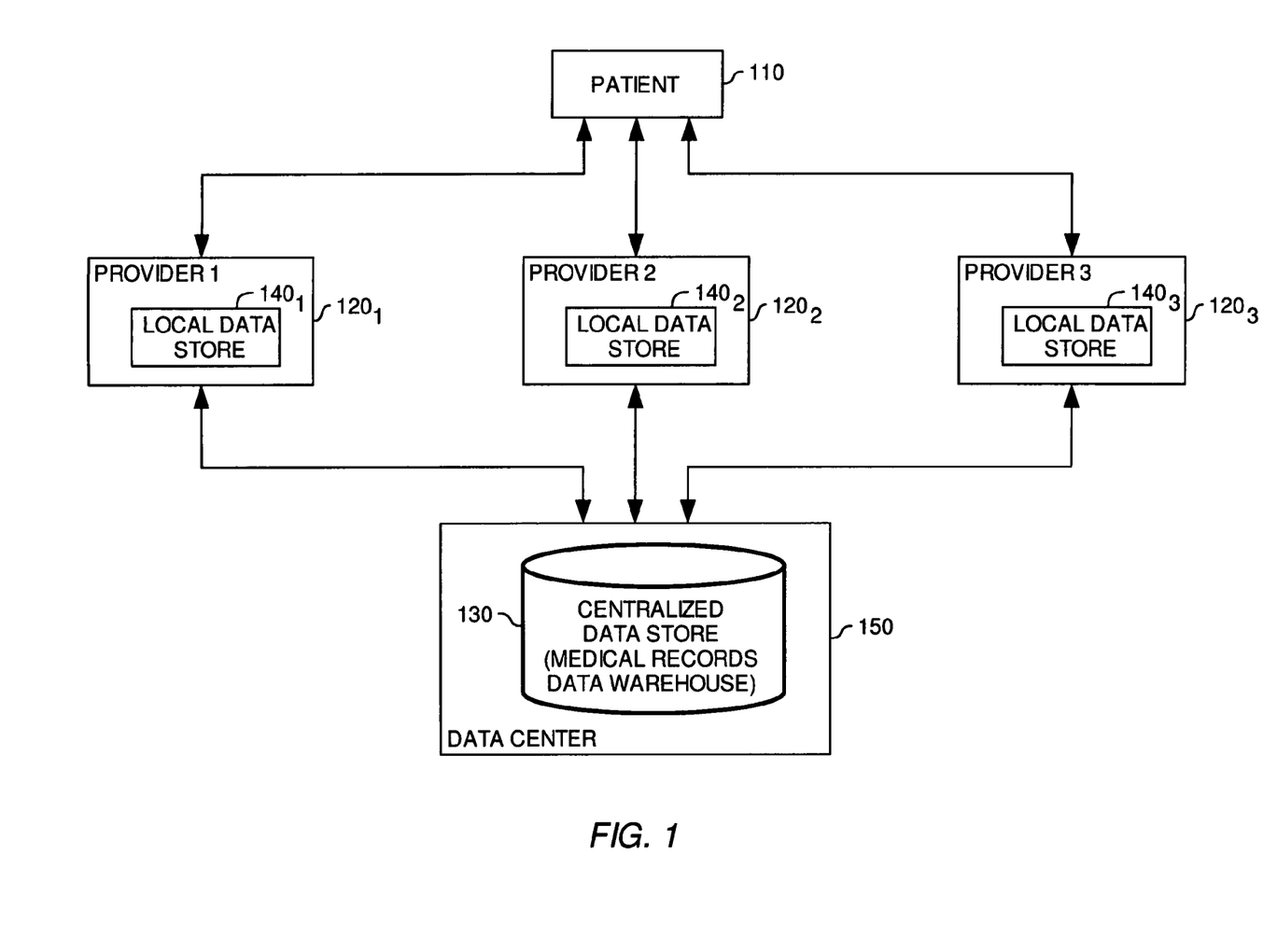
FIG. 1 is a block diagram illustrating the interaction between an individual and a number of health care providers that may generate electronic healthcare records, according to one embodiment of the invention.

FIG. 1 is a block diagram illustrating the interaction between an individual and a number of health care providers that may have shared access to electronic healthcare records, according to one embodiment of the invention. As shown, an individual 110 may interact with providers $120_1$, $120_2$, and $120_3$ (three shown only by way of example) to receive some form of treatment or care for which electronic records may be created and stored in centralized data store 130, or stored in a local data store 140 associated with the provider generating the electronic records.

Each of the providers $120_1$, $120_2$, and $120_3$ represent any individual, entity, or organization that provides health care related goods or services to, or on behalf of, the individual 110. Representative examples of a health care provider 120 include traditional treatment providers, such as the private practice offices of a physician, a clinic, a hospital, and a university medical school or research facility. However, providers 120 may also represent other health-care related entities such as a pharmacy or a physical therapy center. More generally, the providers 120 represent any entity with access to at least some the records available from centralized data store 130 and/or that maintains a local data store 140.

In one embodiment, a provider 120 may create and store electronic healthcare records in a local data store 140. For example, during a treatment encounter between a patient and a physician, a variety of electronic healthcare records may be created. As used herein, "electronic healthcare records" or "electronic records" may include data generated from doctor visits, lab tests, hospital stays, clinical trials, diagnoses (including self-diagnoses), prognoses, etc. More generally, electronic healthcare records include any information or data that may be represented in a digital form and stored in a computer database. Typically, providers 120 (e.g., hospitals, clinics, and private practice groups, etc.) use practice management software to create, store, manage, and access to electronic healthcare records regarding an individual 110. In one embodiment, such electronic healthcare records may be stored in a local data store 140. As shown, each of the providers 120 has access to its own local data store 140. Further, each of the providers 120 may have access to the electronic healthcare records created by one of the other providers and stored in the local data store 140 associated with the other provider. For example, provider 120$_1$ may have access to the local data stores 140$_2$ and 140$_3$. Thus, each local data store 140 may provide a node within a larger database federation.

Additionally, some electronic healthcare records may be stored in the centralized data store 130. In one embodiment, the centralized data store 130 is operated and managed using data center 150. Generally, data center 150 provides a facility designed to house and operate the computer systems and communications equipment required to provide highly reliable access to the electronic healthcare records stored by the data center 150. The data center 150 is designed to ensure that the centralized data store 130 is available to process requests from providers 120 for electronic healthcare records.

Figure 2:
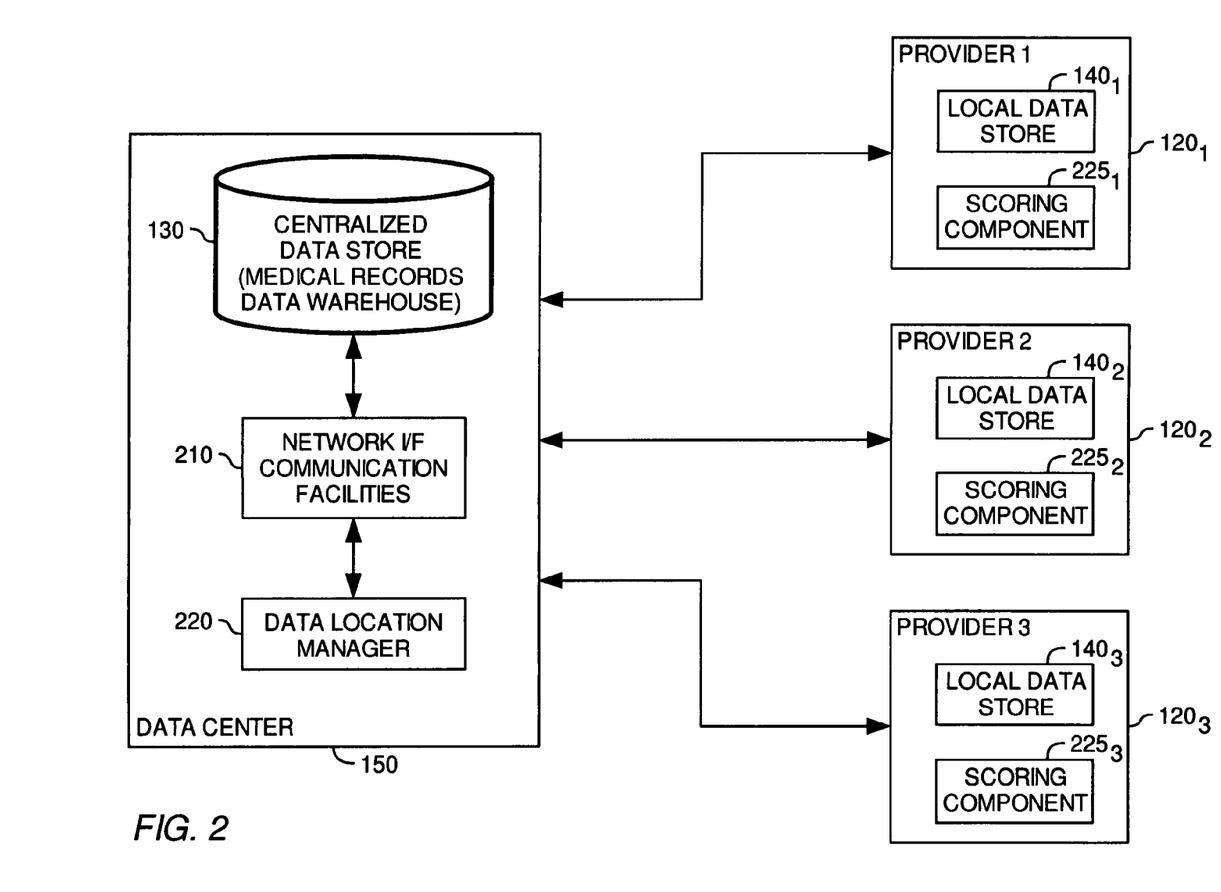
FIG. 2 is a block diagram illustrating a data center used to centralize access to at least some electronic healthcare records, according to one embodiment of the invention.

FIG. 2 is a block diagram illustrating a data center 150 used to centralize access to at least some electronic healthcare records, according to one embodiment of the invention. As shown, the data center 150 includes network communication facilities 210, a data location manager 220, and a centralized data store 130. The network communication facilities 210 provide the appropriate network communication systems allowing providers 120 to communicate with the data center 150. For example, the providers may communicate with the data center to submit records for deposit, submit requests for records, and respond to data relocation requests (e.g., a request to promote a specified electronic record). Further, providers 120 may transmit relocation events to the data location manager 220. As described in greater detail below, a relocation event may cause the data location manager 220 to reevaluate the distribution of electronic records between the centralized data 130 store and local data nodes 120.

As shown, the providers 120 communicate with data location manager 220 to locate electronic records regarding a particular individual. In one embodiment, some records related to a particular individual may be maintained in centralized data store 130 to ensure that providers 120 have reliable and prompt access to records deemed to be of significance. Similarly, the local data store 140 maintained by a particular provider 120 may be used to store records deemed to not be of enough import so as to require guaranteed access availability.

In one embodiment, the centralized data store 130 may include a plurality of independent partitions. Each partition may use a different collection of data location policies 310 to decide which electronic records should be stored in a respective partition. Doing so may ensure that unexpected increase in the proportion of one type of electronic records in the data center 150 will not cause others to be evicted. Additionally, partitions may be dedicated to (or "rented") to one of the providers 120, either permanently or for limited periods. In some situations, a provider 120 may desire to rent a partition from the data center 130 and to select which electronic records to store in the rented partition. Accordingly, provider 120 is shown with a record scoring component 225. In one embodiment, the provider 120 uses the record scoring component 225 to determine whether an electronic healthcare record should be submitted for storage in the centralized data store 130. For example, a provider 120 may operate multiple clinics or hospitals within a given region and desire to ensure that certain records generated at each physical location are stored in the centralized data 130. Another scenario includes a provider 120 temporarily "renting" a partition in the centralized data store 130 in preparation for a scheduled down time, e.g., local system upgrade/maintenance. Still another scenario includes renting a small permanently allocated partition in order to guarantee to an individual that his/her electronic records information will be always readily available (e.g., to an individual that pays a premium fee).

Figure 3:
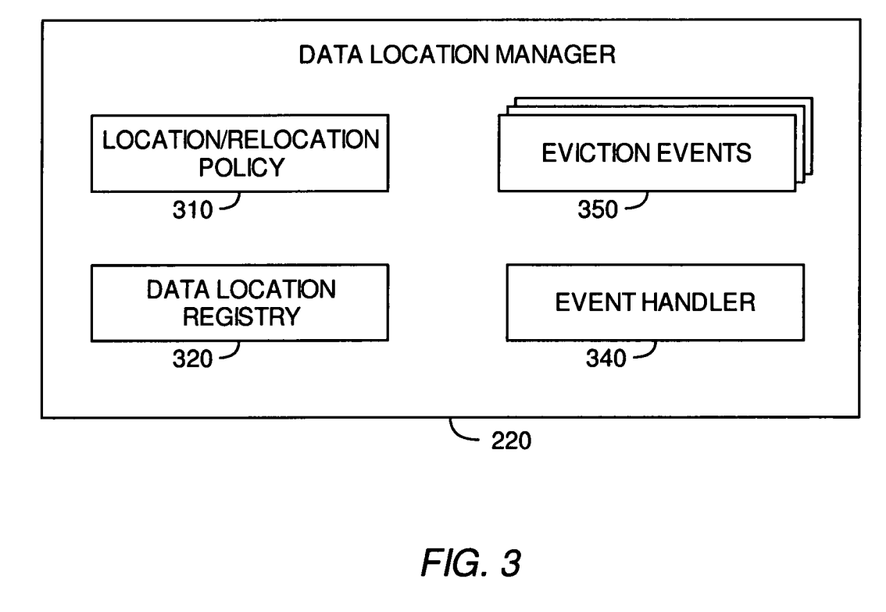
FIG. 3 is a block diagram further illustrating a data location manager configured to locate, and relocate, electronic healthcare records between a centralized data store and one or more distributed data nodes, according to one embodiment of the invention.

FIG. 3 is a block diagram further illustrating a data location manager configured to determine where to locate (and relocate)) electronic medical records stored by both a centralized data store 130 and one or more local data stores 140, according to one embodiment of the invention. As shown the data location manager 230 includes data relocation policies 310, data record registry 320, event handler 340, and scheduled eviction events 350. Although each of the components 310-350 are shown internal to the data location manager 230, some, or all of these components may be provided as services to the data location manager 230 (e.g., in an environment that includes a number of interacting client/server processes).

The relocation policies 310 describe conditions when electronic records should be removed from the one of the distributed local data stores 140 to the centralized data store 130, or vice versa. In one embodiment, relocation policies 310 are also used to provide an initial determination whether an electronic record will be stored in the centralized data store 130. Any number of different of policies is contemplated. Generally, however, each policy may evaluate an electronic record to determine whether it should be stored in the central data store 130. Further, multiple policies may be used to evaluate a given electronic record. In such case, a given access policy may specify a weighting factor used to provide a "score" for an electronic record. In such a case, the scores from multiple policies may be used to determine whether a given data item should be stored in the centralized data store 130. For example, a scoring algorithm may simply sum up the scores for each applicable policy and determine whether a record under consideration is above a threshold required for storage in the centralized data store 130. The following paragraphs provide a non-exhaustive list of several exemplary data relocation policies 230. Each policy may be used to determine whether a given record should be promoted (or evicted) from the centralized data store 130:

Data-Type Based Policies:

A location policy may identify certain types of electronic records that should be stored in the centralized data store 130. An example includes a policy specifying that patient continuity of care records should always be stored in the centralized data store. Another example includes a policy specifying that records of prescription histories or records indicating an allergic reaction to some medication should always be stored in the centralized data store 130.

Data Attribute Policies:

A location policy may identify attributes of certain electronic records. An example includes a policy that causes certain electronic records for patients diagnosed with a specific diagnosis or condition to be stored in the central data store 130, when without such a diagnosis, the electronic records would not be selected for the centralized data store 130. For example, blood sugar tests results are typically of greater importance for individuals diagnosed with diabetes then for individuals without diabetes. In such a case, an access policy may specify a higher score for blood sugar tests associated with individuals diagnosed with diabetes. Or may simply specify that such records are always promoted to the central data store 130.

Policies Based on Data Center Agreements:

Policies may be specified in a service level agreement for a given data store, or on observed performance and accessibility to a given data store. For example, a record location policy could specify that data records from a local node 140 should be relocated into a centralized data store 130 if service level commitments fell below some threshold, or if the observed performance or reliability of the local data store 130 degraded below a defined minimum. Doing so would help limit the impact of a particular local data store 140 experiencing some form of technical problems responding to requests for electronic records.

Event-Triggered Policies:

Event triggered relocation policies may specify when a relocation determination should be made for electronic records regarding a particular individual, based on the occurrence of some contemporaneous event. For example, a relocation policy may specify which electronic records data to promote to the centralized data store 130 when a patient schedules an appointment with a general practitioner, when a patient is admitted to the an emergency room or hospital, or even in anticipation of such events such as when an ambulance is dispatched to the home of a known individual. In one embodiment, when the data location manager 220 is notified of an event, the data records of the individual may be revaluated to determine whether to relocate a set of electronic records to the central data store. The relocation may be permanent or temporary.

For example, if an event-triggered policy specified that all records related to an individual should be relocated to the central data store 130 based on an admission to an emergency room, then such a policy could further specify that after a period of two weeks, any relocated records should be evicted. Doing so would allow for a dynamic set of records in the data store 130, making it more likely that when a patient sought follow-up care after an emergency room visit that most, if not all, records regarding the individual are available to health care providers 120 from the high-availability data store 130. At the same time, after the probability that a provider 120 will request records regarding this patient drops off, the records may be removed from the data store 130.

Individual Based Policies:

A data location policy may be based on individual and/or payer sensitivity to the history of a particular individual. For example, an individual that is willing to pay to have his or her own health records stored in a central data store for universal accessibility could do so. Similarly, a healthcare insurer (payer) who determines that an insured individual is at a higher risk for emergency care or multiple healthcare provider interactions may select to have the electronic records related the individual more widely available and accessible to healthcare professionals, allowing better treatment.

Infrastructure Based Policies:

A relocation policy may be based on space available and priority of each type of data. Using an infrastructure based policy; the centralized data store 130 may store as much information as possible and when full, may be configured to evict electronic records determined to be lower in priority to make room for higher priority data. Electronic records in the centralized data store would be ranked according to a scoring algorithm involving other types of policies and would be evicted in reversed rank order (e.g. lowest ranked data would be evicted first).

Planned Encounter Policies:

A relocation policy may be based on specific types of patient/provider encounters. For example, when a patient schedules an appointment to be treated by a cardiac specialist, electronic records regarding any EKG tests, or records related to a primary care physician's decision to refer the individual to the cardiac specialist may be relocated to the centralized data store 130. Like the case of event driven data relocation, planned encounters may be used to temporarily relocate electronic records to the centralized data store 130.

In one embodiment, some, all, or other event location and relocation policies described above may be used to by a data location manager 230 to evaluate electronic data records based on a set of scoring criteria. Electronic records with a score above a threshold level would be promoted to being stored in the centralized data store 130, even if only temporarily. In such a case, a relocation policy 310 may have an associated weighting factor. For example, each policy relevant to a particular record may be used to score the record, and an overall score calculated as a sum of all relevant policy scores.

Alternatively, some data location policies may specify that a given record should always be stored in the centralized data store 130. For example, records related to any allergic reactions an individual is known to have may always be stored in the centralized data store 130. Another example includes an individual who desires to rent a partition from the data center 150 to ensure that his/her records are always available. In such a case, a relocation policy 310 may be specific to records related to the individual, and always store such records in the centralized data store 130.

As shown in FIG. 3, data relocation manager 230 includes a data location registry 320. In one embodiment, the data relocation manager 230 component may be used to specify the existence and current location of electronic records. For example, the data location registry 230 may provide an index regarding all of the electronic records available in either the centralized data store 130, or one of the local data stores 140. The event handler 340 may be configured to process relocation events. As described above, relocation events may be triggered whenever an event occurs making it appropriate to reconsider the location of at least some electronic records related to a particular individual based on the record relocation policies 310. Eviction events 350 represent a list of records that have been promoted to the centralized data store 130 for a temporary amount of time. When the eviction time is reached, the record may be evicted from the centralized data store 130. When this occurs, the evicted record remains available from the appropriate local data store 140.

Figure 4:
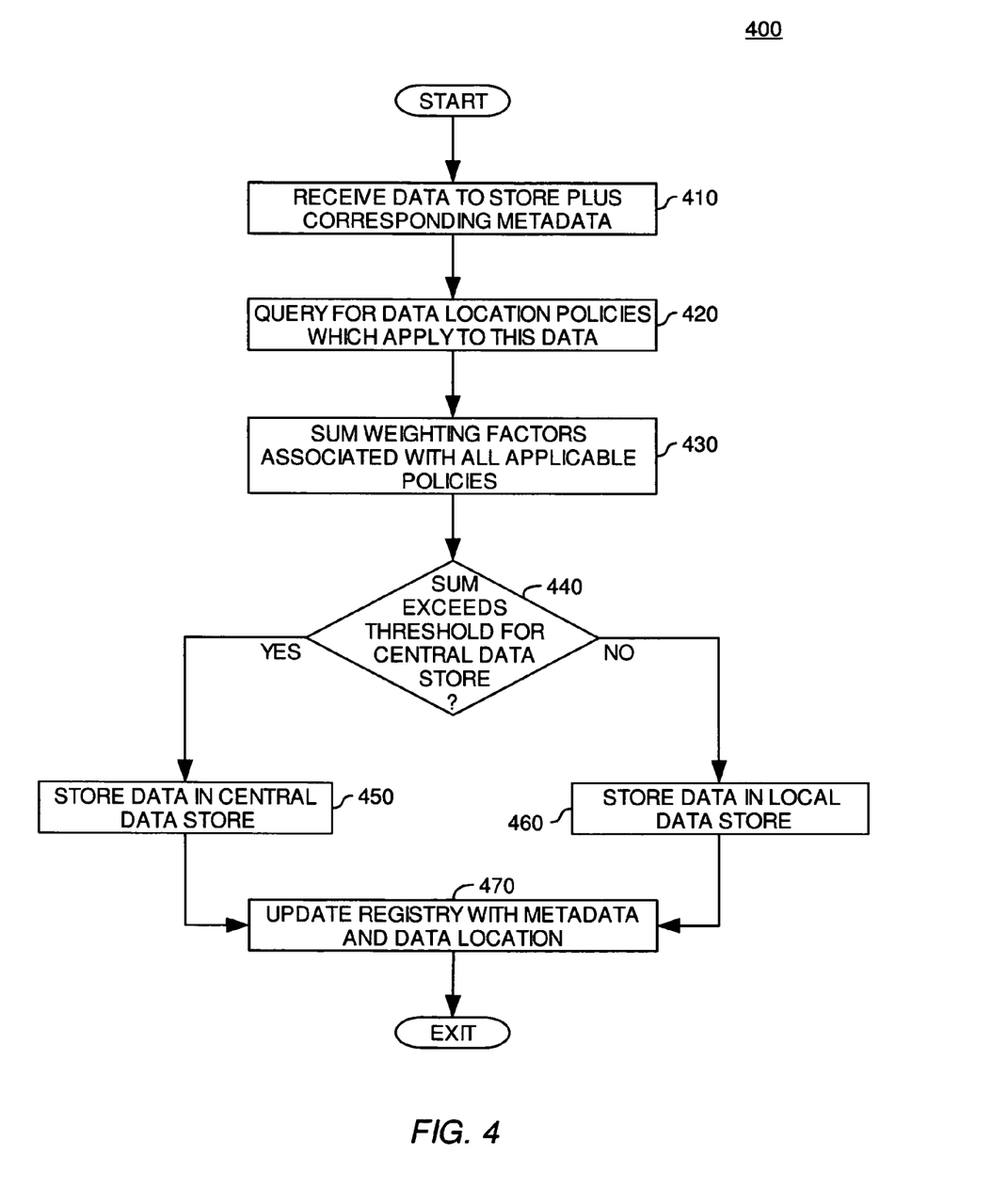
FIG. 4 is a flow chart illustrating a method for determining a location to store an electronic healthcare record, according to one embodiment of the invention.

FIG. 4 is a flow chart illustrating a method for determining a location to store an electronic record, according to one embodiment of the invention. At step 410, the data location manager 220 may receive an electronic record from one of providers 120. Along with the substantive electronic record, the data location manager 220 may also receive any additional information required by the relocation policies 310 to determine a location for the record. At step 420, the data location manager 220 may determine which data location policies 310 apply to the electronic record received at step 410. For example, some policies may only apply to test results, while others may apply to images data such as x-ray films or MRI images. Other policies may apply globally to any electronic record submitted to the data location manager 220 for storage.

At step 430, the weighting factors associated with all applicable policies are used to calculate a location score for the electronic record under consideration. Once a location score is calculated, at step 440, the data location manager 220 determines whether the record should be promoted to the centralized store 130, or should remain stored in the local data store 140. For example, the data location manager 230 may determine whether the data location score for the record exceeds the threshold required to for promotion to the centralized data store 130. Alternatively, a policy may specify that certain records (e.g., records indicating an allergic reaction) are always promoted for storage in the centralized data store 130.

At step 450, if the location score exceeds the threshold, then the record is stored in the centralized data store 230. Otherwise, at step 460, the record is (or remains) stored in the appropriate local data store 140. At step 470, the data location registry 320 may be updated to indicate whether the record under consideration was promoted to storage in the centralized data sore 130 or will be stored in one of the local data stores 140.

Figure 5:
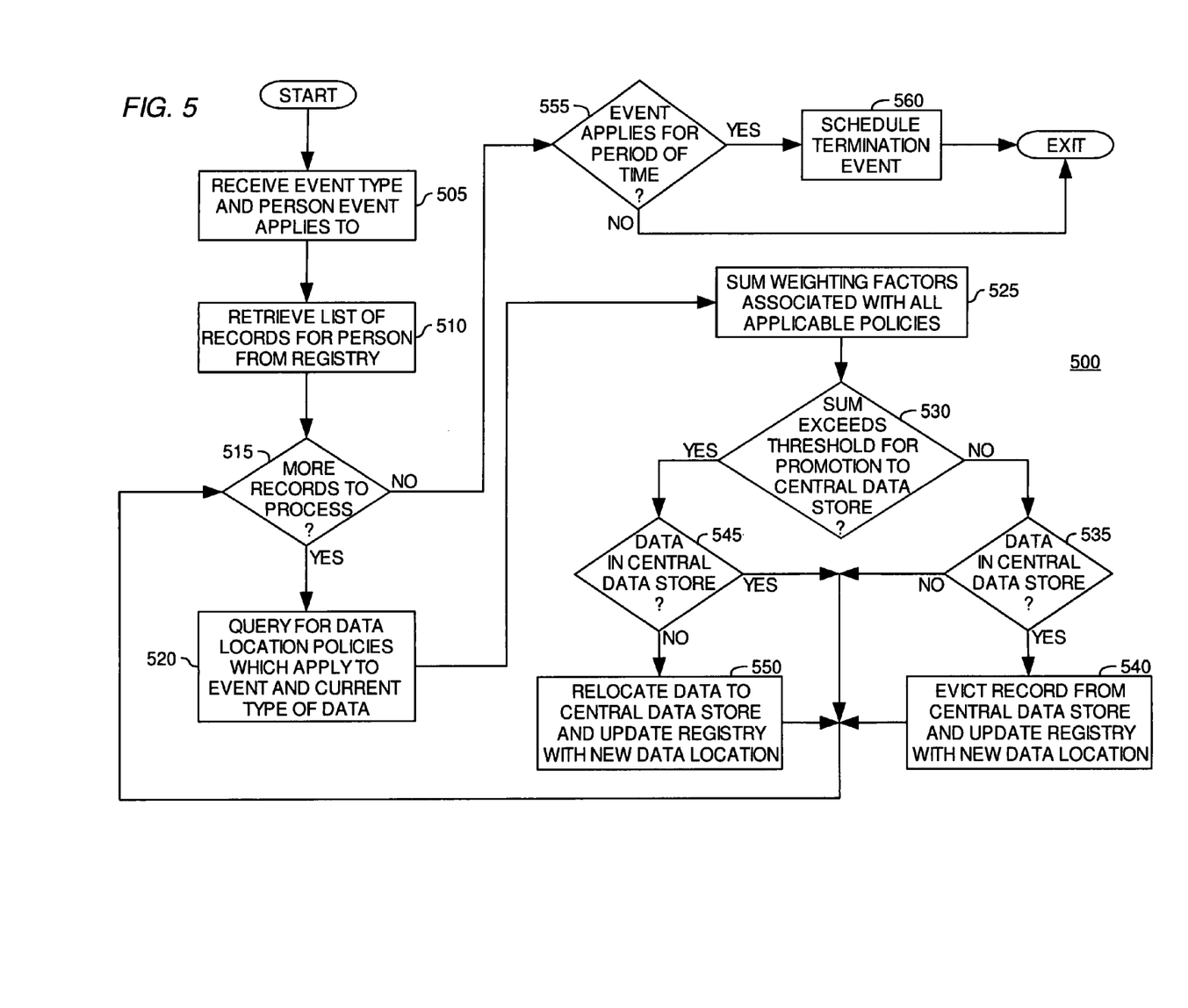
FIG. 5 is a flow chart illustrating a method for relocating at least some electronic healthcare records related to a particular individual, based on a data relocation policy, according to one embodiment of the invention.

FIG. 5 is a flow chart illustrating a method for relocating at least some electronic records related to a particular individual, based on a data relocation policy, according to one embodiment of the invention. In one embodiment, the method 500 may be performed by event handler 340 in response to the occurrence of one of the relocation events described above. At step 505, the event handler 340 receives the event type and indication of the relevant individual. At step 510, the event handler 340 may be configured to consult the data location registry 320 to retrieve a list of electronic records stored in the centralized data store 130 and local data stores 140 that pertain to the individual identified in the relocation event.

At step 515, a loop beings that includes step 520-550. For each pass through this loop, the data location manager 230 may select one of the records associated with the individual and determine whether the record should be promoted to (or evicted from) the centralized data store 130. At step 520, the event handler 340 may determine which data location policies 310 apply to the electronic record under consideration based on the event type identified at step 505. At step 525, each applicable relocation policy is used to calculate a location score for the record under consideration.

At step 530, the event handler 340 determines whether the location score exceeds the requirement for promotion to the central data store 130. If not, then a determination is made whether the record is currently in the centralized data store 130 (step 535). If so, at step 540 the record is evicted from the centralized data store, and the data location registry 320 is updated to reflect the change in record location. Otherwise, the record is not in the centralized data store 130, and does not qualify for promotion. In such case, no action is required, and the method 500 returns to step 515 to evaluate additional electronic records for relocation. Returning step 530, if the event handler 340 determines that the location score for the record under consideration exceeds the threshold required for promotion, then at step 545 a determination is made whether the record is already in the centralized data store 130. If not, the record is promoted to the centralized data store, and the data location registry 320 is updated with the new data location for the record.

The method 500 then returns to step 515 where the event handler 340 determines whether additional records need to be evaluated for relocation. If so another record identified at step 510 is evaluated according to the loop that includes steps 520-550. After evaluating all of the relevant electronic records, the event handler 340 may be configured to determine whether the particular event being processed applies for a limited period of time (step 555). For example, as described above, some events may only trigger a temporary promotion to the centralized data store 130. If so, then the event handler 340 may be configured to schedule an eviction event 350 for any electronic records promoted to the centralized data store 130 (step 560). Otherwise, the method 500 concludes.

As described above, electronic records may be distributed between a high-availability, fault-tolerant data store and a set of distributed nodes of a data federation. In one embodiment, a set of data location policies 310 are used to select whether a record should be located in the high-availability data store 130. However, events may occur making the availability of an individual's electronic records of critical concern. In such case, relocation policies 310 may identify some records that should be promoted for storage in the in the high-availability data store 130.

The data relocation policies may define when centralized data access is considered to be most appropriate. Thus, embodiments of the invention acknowledge that centralized storage of all data may be impractical, but recognize that some electronic records, at least in some circumstances, should be given the advantage of predictable and reliable quality of service available from a centralized store managed by a data center, as compared to the quality of service typically provided by highly distributed or federated database systems.

While the foregoing is directed to embodiments of the present invention, other and further embodiments of the invention may be devised without departing from the basic scope thereof, and the scope thereof is determined by the claims that follow.

What is claimed is:

1. A computer-implemented method of selecting a location to store an electronic record, the method comprising:
   receiving the electronic record from a first health care provider, of a plurality of health care providers, wherein each of the plurality of health care providers maintains a local data store of electronic records, and wherein the plurality of health care providers have shared access to a centralized data store;
   retrieving a set of data location policies used to determine which electronic records are to be accessible from the centralized data store;
   evaluating the electronic record, based on the data location policies, to determine whether the electronic record should be accessible from the centralized data store or from the local data store of the first health care provider;
   if so, storing the electronic record in the centralized data store;
   if not, storing the electronic record in the local data store of the first health care provider; and
   updating a data location registry to indicate the location of the electronic record.

2. The method of claim 1, further comprising:
   receiving an indication of a relocation event, wherein the relocation event specifies an event type and an individual associated with the relocation event;

identifying the electronic records listed in the data location registry regarding the individual;

retrieving one or more relocation policies associated with the relocation event;

for each identified electronic record, determining whether to relocate the electronic record, based on the data relocation policies; and for any electronic records determined to be relocated, relocating such electronic records and updating the data location registry to indicate the location of the electronic record.

3. The method of claim 2, wherein determining whether to relocate the electronic record comprises, determining to relocate the electronic record between the one of the plurality of local data stores and the centralized data store.

4. The method of claim 2, wherein the relocation event is triggered in response to the individual associated with the relocation event seeking treatment from one of the plurality of health care providers.

5. The method of claim 2, wherein the relocation event is based on an infrastructure based policy specifying a distribution of electronic records between the centralized data store and the plurality of local data stores.

6. The method of claim 2, wherein the relocation event is triggered in response to a change in a capacity of the centralized data store to provide access to electronic records.

7. The method of claim 2, wherein electronic records are relocated to the centralized data store for a specified period of time.

8. The method of claim 1, wherein the centralized data store provides a plurality of partitions, wherein each partition stores a set of electronic records, according to a set of data location policies associated with a given partition.

9. A computer-readable medium containing a program which, when executed, performs an operation for selecting a location to store an electronic record, the operation comprising:

receiving the electronic record from a first health care provider, of a plurality of health care providers, wherein each of the plurality of health care providers maintains a local data store of electronic records, and wherein the plurality of health care providers have shared access to a centralized data store;

retrieving a set of data location policies used to determine which electronic records are to be accessible from the centralized data store;

evaluating the electronic record, based on the data location policies, to determine whether the electronic record should be accessible from the centralized data store or from the local data store of the first health care provider;

if so, storing the electronic record in the centralized data store;

if not, storing the electronic record in the local data store of the first health care provider; and updating a data location registry to indicate the location of the electronic record.

10. The computer-readable medium of claim 9, wherein the operations further comprise:

receiving an indication of a relocation event, wherein the relocation event specifies an event type and an individual associated with the relocation event;

identifying the electronic records listed in the data location registry regarding the individual;

retrieving one or more relocation policies associated with the relocation event;

for each identified electronic record, determining whether to relocate the electronic record, based on the data relocation policies; and for any electronic records determined to be relocated, relocating such electronic records and updating the data location registry to indicate the location of the electronic record.

11. The computer-readable medium of claim 10, wherein determining whether to relocate the electronic record comprises, determining to relocate the electronic record between the one of the plurality of local data stores and the centralized data store.

12. The computer-readable medium of claim 10, wherein the relocation event is triggered in response to the individual associated with the relocation event seeking treatment from one of the plurality of health care providers.

13. The computer-readable medium of claim 10, wherein the relocation event is based on an infrastructure based policy specifying a distribution of electronic records between the centralized data store and the plurality of local data stores.

14. The computer-readable medium of claim 10, wherein the relocation event is triggered in response to a change in a capacity of the centralized data store to provide access to electronic records.

15. The computer-readable medium of claim 10, wherein electronic records are relocated to the centralized data store for a specified period of time.

16. The computer-readable medium of claim 9, wherein the centralized data store provides a plurality of partitions, wherein each partition stores a set of electronic records, according to a set of data location policies associated with a given partition.

17. A system for storing electronic records, comprising:

a centralized data store having respective communication links to a plurality of local data stores each maintaining electronic records, wherein each of the local data stores is maintained by a respective health care provider, each having access to electronic records stored in the centralized data store; and a data access manager configured to determine whether to store an electronic record, received from a first one of the health care providers, in the centralized data store, wherein the data location manager is configured to determine whether to store the electronic record in the centralized data store by:

retrieving a set of data location policies used to determine which electronic records are to be accessible from the centralized data store, evaluating the electronic record, based on the data location policies, to determine whether the electronic record should be accessible from the centralized data store or from the local data store of the first health care provider, if so, storing the electronic record in the centralized data store, if not, storing the electronic record in the local data store of the first health care provider, and updating a data location registry to indicate the location of the electronic record.

18. The system of claim 17, wherein the data location manager is further configured to:

receive an indication of a relocation event, wherein the relocation event specifies an event type and an individual associated with the relocation event;

identify the electronic records listed in the data location registry regarding the individual;

retrieve one or more relocation policies associated with the relocation event;

for each identified electronic record, determining whether to relocate the electronic record, based on the data relocation policies; and for any electronic record determined to be relocated, relocating the electronic records and updating the data location registry to indicate the location of the electronic record.

19. The system of claim 18, wherein determining whether to relocate the electronic record, determining to relocate the electronic record between the one of the plurality of local data stores and the centralized data store.

20. The system of claim 18, wherein the relocation event is triggered in response to the individual associated with the relocation event seeking treatment from one of the plurality of health care providers.

21. The system of claim 18, wherein the relocation event is based on an infrastructure based policy specifying a distribution of electronic records between the centralized data store and the plurality of local data stores.

22. The system of claim 18, wherein the relocation event is triggered in response to a change in a capacity of the centralized data store to provide access to electronic records.

23. The system of claim 18, wherein electronic records are relocated to the centralized data store for a specified period of time.

* * * * *